United States Patent [19]

Madrange et al.

[11] 4,122,159

[45] Oct. 24, 1978

[54] AEROSOL FOAMING COMPOSITIONS

[75] Inventors: Annie Madrange, Saint Germain en Laye; Jean Maës, Vitry sur Seine; Pierre Meurice, L'Isle Adam, all of France

[73] Assignee: L'Oreal, Paris, France

[21] Appl. No.: 799,689

[22] Filed: May 23, 1977

[30] Foreign Application Priority Data

Feb. 24, 1977 [FR] France .................. 77 05350

[51] Int. Cl.$^2$ ................ A61K 7/00; A61K 7/09; C09K 3/30
[52] U.S. Cl. .................. 424/45; 252/305; 424/47; 424/71

[58] Field of Search .................. 424/45, 47, 71; 252/305

[56] References Cited

U.S. PATENT DOCUMENTS

| 3,574,118 | 4/1971 | Baker | 252/305 |
|---|---|---|---|
| 3,826,682 | 7/1974 | Leibowitz | 252/305 |
| 3,970,584 | 7/1976 | Hart et al. | 424/47 |

*Primary Examiner*—Sam Rosen
*Attorney, Agent, or Firm*—Brisebois & Kruger

[57] ABSTRACT

Aerosol foam compositions which have improved stability and foaming containing 2–14% liquified gas and nitrous oxide propulsive agent, 0.2–6% of a tensio-active amphoteric foaming agent, and 0.2–3% tertiary amino oxide.

18 Claims, No Drawings

AEROSOL FOAMING COMPOSITIONS

SUMMARY OF THE INVENTION

The use of foaming compositions for body and hair care, intended to be dispensed in the form of foam from a conditioning container of the aerosol bomb type are well known. One is able, for example, to cite in this regard, the packaging in a pressurized can of foaming shaving creams or of reducing agents for a cold hair permanent. These familiar foaming preparations contain, in combination with the active dispensed materials, a propelling agent such as a hydrocarbon, preferably halogenated, found to be at a liquid-vapor state at temperatures of use, under a relatively low pressure, on the order of several bars.

In the field of cold permanents of this type, there are two types of foaming preparations. One of these is described in the U.S. Pat. No. 3,099,603: it concerns a packaged composition in a pressurized can which produces a foam having the peculiarity of breaking down very rapidly to become a liquid. The application to the hair of the reducing agent contained in this preparation is made in the form of an unstable foam which almost immediately transforms itself into a liquid whose wetting power is higher than foam and which can, consequently, better impregnate the locks of hair. The inconvenience which this kind of foam presents is essentially lack of stability and, consequently, running soon after it is dispensed. It is not possible to obtain with this preparation a firm foam which can cover the head of hair uniformly without running during the major part of the time required for treatment.

A second kind of foaming composition, packaged in a pressurized can and used also as a permanent wave reducing agent, is applied in liquid form on the hair to insure good saturation. Once the liquid is released, it produces a relatively stable foam, but this foam posesses, after expansion, poor hair wetting characteristics. This foaming preparation has two disadvantages: that of being applied in the liquid state, which produces certain unpleasantness due to the fact that the product can run at the moment of its application and cause, for example, eye irritation or stains on clothing; and that of having a reduced effectiveness because of its poor wetting characteristics, after it foams.

The present invention has for an object the remedying of previously mentioned disadvantages and inconveniences and, to this end, provides a new foaming composition permitting the obtaining of a foam which posesses novel properties due to the combination of increased stability during initial dispensing from the pressurized container and great foam production.

The composition according to the invention, while it contains a reducing agent for hair permanents, is capable of producing a stable foam, which penetrates progressively into the locks of hair rolled on the hair curlers. During the entire duration of the treatment, the foam stays well in place on the hair and its volume decreases only very slowly, the texture of the foam modifying itself only gradually. Due to its exceptional foaming power, the impregnation of the reducing agents in the foam occurs gradually in all the locks of hair. Moreover, the foam that is obtained according to the invention, initially presents a very dense texture, that is to say a high mass per unit volume on the order of 0.05 g/cm$^3$ to 0.15 g/cm$^3$. Thus, while it entirely covers the head of hair during the treatment, the foam acts as an insulating cap, which has the effect of keeping the hair at the temperature necessary for a good reducing action of the permanent, and without which it would be necessary to use a plastic cap to insulate the hair from the outside.

The combination of the properties of stability and of wetting of foams obtained with the compositions according to the invention is valuable not only in the field of reducing agents for cold permanents but also in other areas such as that of permanent fixing solutions, depilatories, hair-straightening solutions and dyes.

The present invention has then for its object the new industrial product composed of a conditioned foaming composition inside a pressurized container of the aerosol bomb type to be dispensed in the form of a foam, the composition containing in combination a propelling agent, a foaming product, and an active conditioning product, characterized by the fact that it contains, on the one hand, from 2 to 14% propulsive agent and, on the other hand, as a foaming product from 0.2 to 6% at least of a tensio-active amphoteric agent and from 0.2 to 3% at least of tertiary amino oxide, all the percentages previously mentioned being expressed in relation to the weight of the nonpropulsive part of the composition. The propelling agent used contains a mixture of liquified gas and of nitrous oxide (N$_2$O) saturating the whole of the liquid phase, the mixture of liquified gas being taken from the group consisting of:

a. a mixture of dichlorodifluoromethane known under the commercial designation of "Freon-12" and of dichlorotetrafluoroethane known under the commercial designation of "Freon-114" containing contingently at least one nonhalogenated alkane taken from the group formed by butane, propane and isobutane;

b. a mixture of butane and of propane containing contingently isobutane;

c. a mixture of isobutane and of propane.

It is meant by "nonpropulsive part" in the present description and the claims, the part of the liquid phase of the composition that does not include the liquified propulsive agent.

Among the possible amphoteric tensio-active agents, which are particularly appropriate for the foaming composition according to the invention, are:

a. agents with a betainic structure such as, for example, an amidoalkylbetaine corresponding to the following formula:

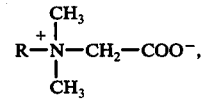

in which R represents a residue derived from fatty acids containing from 12 to 18 carbon atoms;

b. agents with imidazolinic structure such as, for example, the compounds of the formula:

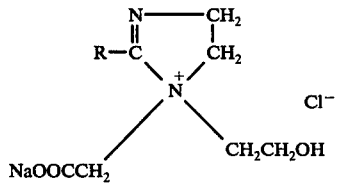

in which R is the hydrocarbon residue derived from coprah, and such a composition is sold by Society REWO under the name of "STEINAPON AM2C";

c. agents with betainic and imidazolinic structure such as, for example, hydroxyethyl-1 alkyl-2 carboxymethyl-3 imidazolinium betaine;

d. agents with an aminimide structure such as, for example, the 1,1-dimethyl-1,6-(2-hydroxypropyl) hexadecylimide;

e. agents with aminopropionate structure such as, for example, sodium N-alkyl β-aminopropionate in which the alkyl is the hydrocarbonated residue of the fatty acids from coprah and the laurylaminopropionate of triethanolamine;

f. agents with an asparaginous structure such as those described in the French Pat. No. 1,344,212 and in its certificate of addition Ser. No. 89,478 filed in the name of the applicant. Such compositions correspond to the following formula:

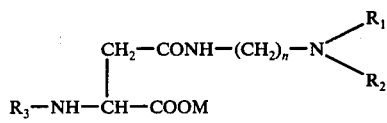

in which $R_1$ and $R_2$ are lower alkyl radicals able to contain up to 4 carbon atoms, $n$ is an integer 2 to 5 preferably 2 or 3, $R_3$ designates an aliphatic hydrocarbonated residue containing from 10 to 18 carbon atoms, and M is hydrogen, sodium, potassium or ammonium.

Among the tertiary amino oxides which are used in the composition according to the invention, one can mention the alkyldimethylamino oxides, in which the alkyl radical is a lauric, cetylic, myristic or stearic residue; bi-(2-hydroxyethyl)coprahamino oxide; and bi-(2-hydroxyethyl)laurylmyristylamino oxide.

In the preferred embodiment of the foaming compositions according to the invention, the mixture of liquified gas is saturated with $N_2O$, the equalized pressure, after saturation, being between 4 and 8 bars; the relative proportions of the mixture dichorofluoromethane/dicholorotetrafluoroethane/alkane are between 0/100/0&25/25/50, the relative proportions of the mixture butane/propane/isobutane are between 90/10/0 and 25/25/50; the relative proportions of the mixture isobutane/propane are between 100/0 and 40/60.

According to the invention the foaming composition is able to be advantageously used in hair treatment, as a reducing agent for cold permanents. For this application, the foaming composition contains as an active product, from 1 to 11% of at least one thiol and as a foaming product, from 0.2 to 6% of at least one amphoteric tensio-active agent mentioned above, and from 0.2 to 3% of at least one of the tertiary amino oxides mentioned above, these percentages being expressed by weight in relation to the weight of the nonpropulsive part of the composition. The thiol used is selected from the group consisting of thioglycolic acid, thiolactic acid, thioglycerol or a mixture of these; the preferred amount of thioglycolic acid is between 3 and 11%, the preferred amount of thiolactic acid is between 1 and 6% and the preferred amount of thioglycerol is between 4 and 8%, these percentages being expressed by weight in relation to the weight of the non-propulsive part of the composition.

The foaming composition according to the invention can also be used advantageously in the treatment of hair as a fixative agent for permanents. In this new use, the foaming composition contains, by virtue of its foaming product, from 0.2 to 6% of at least one of the amphoteric tensio-active agents above mentioned, from 0.2 to 3% of at least one tertiary amino oxide above designated, from 0.15 to 2% of at least one cationic tensio-active agent and by virtue of its active product, from 6 to 10 volumes of $H_2O_2$ or from 8 to 18% of potassium bromate or sodium bromate, these percentages being expressed by weight in relation to the nonpropulsive part of the composition.

Among the cationic tensio-active agents which are used in the permanent fixing solution according to the invention, one can mention:

a. the quaternary derivatives of ammonium, for example: the chlorides of dimethylhydroxyethylalkyl (fat) ammonium; the chloride of cetyltrimethyl-ammonia; the chlorides of dialkyldimethylammonium whose alkyl groups contain 12 to 18 carbon atoms and in particular distearyldimethylammonium chloride;

b. the derivatives of pyridinium, for example: N-stearylcolaminoformylmethylpyridinium chloride; the chlorides of alkylpyridinium in which the alkyl group contains from 12 to 18 carbon atoms.

The foaming composition according to the invention can equally be used in a depilatory composition. For this new application, the composition contains advantageously in combination, as an active product, from 2 to 8% of at least one thiol neutralized totally or in part, for example, by sodium hydroxide, lithium oxide or calcium hydroxide and, as a foaming agent, from 0.5 to 2% of at least one of the amphoteric tensio-active agents mentioned above and from 0.2 to 1.5% of at least one of the tertiary amino oxides mentioned above, these percentages being expressed by weight in relation to the weight of the nonpropulsive part of the composition. Among the thiols particularly useful in such a depilatory foaming composition, one can mention thioglycolic acid, thiolactic acid, thioglycerol or a mixture of these; the amount of thioglycolic acid in relation to the nonpropulsive part is between 2 and 7% by weight, the amount of thiolactic acid is between 2 and 7% and the amount of thioglycerol is between 3 and 8% by weight.

The foaming composition according to the invention can also be used in a hair straightener composition. For this new application, the foaming composition contains advantageously, as a foaming product, from 0.5 to 2% of at least one of the amphoteric tensio-active agents mentioned above and from 0.2 to 1.5% of at least one of the tertiary amino oxides mentioned above; and, as an active product, from 4 to 10% of thioglycolic acid or of thiolactic acid, or from 1 to 5% of sodium hydroxide, lithium oxide, or mixture thereof, these percentages being expressed by weight in relation to the weight of the nonpropulsive part of the composition.

The foaming composition according to the invention is also useful as a neutralizer following a hair straightening procedure. For this new application, the composition contains advantageously, as a foaming product, from 0.5 to 2% of at least one of the amphoteric tensioactive agents mentioned above, from 0.2 to 1.5% of at least one of the tertiary amino oxides mentioned above; from 0.5 to 1.5% of at least one of the cationic tensio-active agents mentioned above; and, as an active product, from 3 to 10% of sodium bromate or potassium bromate or from 6 to 10 volumes of $H_2O_2$, these percentages being expressed by weight in relation to the weight of the non propulsive part of the composition.

The foaming compositions according to the invention are packaged in classical type aerosol bombs, having a dispensing valve. The valve acts jointly, in general, with a pushbutton which the user presses to cause its opening for the ejection of foam through the dispensing tip associated with said pushbutton.

To better understand the present invention, there follows, several examples of nonlimiting applications. In these examples, the percentages are expressed by weight in relation to the total weight of the composition.

EXAMPLE 1

A foaming composition was prepared according to the invention, used as reducing agent for a cold hair permanent. The composition contained 7% propellant. The propellant was a mixture of 60% of "Freon-114" and 40% "Freon-12". The whole of the liquid phase was saturated with nitrous oxide ($N_2O$). The equilibrium pressure of nitrous oxide after saturation was 7 bars at 20° C. The nonpropulsive part of the foaming composition contains:

| Nonpropulsive part | |
|---|---|
| Thioglycolic acid | 10 g |
| Ammonia | 9 g |
| Ammonium bicarbonate | 6.1 g |
| Amphoteric tensio-active agent* | 4 g |
| Lauryldimethylamino oxide | 0.4 g |
| Perfume | qs (sufficient quantity |
| Water -qsp (Quantity sufficient for preparation) | 100 g |

*N,N-diethylaminopropyl-$N^2$-alkyl asparagine (sodium salt) having the following formula R—NH—CH—COONa        $C_2H_5$
         |                   /
         $CH_2$—CO—NH—($CH_2$)$_3$—N
                                   \
                                    $C_2H_5$ R = alkyl residue derived from fatty acids of coprah or tallow (⅔ coprah, ⅓ tallow); this amphoteric tensio-active agent is described in the French patent 1,344,212

EXAMPLE 2

A foaming composition was prepared for use as a fixing agent for cold hair permanents. The composition contained 6% propellant of the same type as that of Example 1. The non-propulsive part of the composition contained:

| Nonpropulsive part | | |
|---|---|---|
| Potassium bromate | 10 | g |
| Amphoteric tensio-active agent* | 2 | g |
| Lauryldimethylamino oxide | 0.3 | g |
| Coprahdimethylammonium chloride | 0.3 | g |
| Citric acid -qsp- pH=6.2 | | |
| Perfume | qs | |
| Water -qsp- | 100 | g |

*Derived from fatty amines of betainic structure produced under the name of "DEHYTON AB 30"

Applied on damp natural hair rolled on curlers, the composition reducing agent of Example 1 produced a very oily foam, which was applied very easily to completely cover hair. This cover served as a cap, which maintained the temperature necessary for a good reducing action on each lock of hair.

After rinsing, the fixing agent composition of Example 2 was applied in the same manner, in such a fashion as to obtain a foam cover permitting good saturation of, and excellent fixation of each curl. After the final rinse, the wave produced was strong and regular from the roots to the tips. The cosmetic state of the hair was very good.

EXAMPLE 3

A foaming composition used as a reducing agent for permanents was prepared. The propulsive agent used was the one used in Example 1. The percentages of the propellant in the composition was 10%. The nonpropulsive part of the foaming composition contains:

| Nonpropulsive part | | |
|---|---|---|
| Thioglycolic acid | 3 | g |
| Thiolactic acid | 2 | g |
| Ammonia | 4 | g |
| Triethanolamine | 3.7 | g |
| Amphoteric tensio-active agent* | 5 | g |
| Bi-(2-hydroxyethyl)lauryl-myristylamino oxide | 0.9 | g |
| Perfume | qs | |
| Water -qsp- | 100 | g |

*Derived from fatty amines with betainic structure, commercially available under the name of: "DEHYTON AB 30"

EXAMPLE 4

A foaming composition was prepared for use as a fixing agent for a permanent. The composition contained 5% by weight of the propellant of Example 1. The nonpropulsive part of the foaming composition contained:

| Nonpropulsive part | | |
|---|---|---|
| Oxygenated water | 8.7 | volumes |
| Laurylamino propionate of triethanol amine | 1.3 | g |
| Cetyldimethylamino oxide | 0.7 | g |
| Cetylpyridinium chloride | 0.9 | g |
| Tartaric acid -qsp- | | |
| pH = 4.5 | | |
| Perfume | qs | |
| Water - qsp- | 100 | g |

The reducing agent composition of Example 3 as well as the fixing agent composition of Example 4 were both used to produce a cold permanent. Applied on damp rolled hair, the reducing agent composition of Example 3 provided an abundant foam which, while remaining stable, penetrated gradually into the rolled curls. Due to the high wetting power of this foam, the impregnation of the reducing agent occurs progressively into all the rolled curls.

After rinsing, the fixing agent composition of Example 4 which was applied in the same manner, provided a good impregnation and a very secure fixation of each lock of hair and thus produced a firm wave.

After a final rinsing, the wave obtained was regular. The hair was in a very beautiful cosmetic state.

EXAMPLE 5

A depilatory foaming composition was prepared containing 7% propellant. The propellant used was the same as in Example 1.

The nonpropulsive part of this foaming composition contained:

| Nonpropulsive part | |
|---|---|
| Cetylalcohol | 7 g |
| Thioglycerol | 7.5 g |
| Myristyldimethylamino oxide | 0.6 g |
| Amphoteric tensio-active agent | 2.2 g |

-continued

| Nonpropulsive part |
|---|
| Urea |
| Calcium hydroxide |
| Oxyethylated lanolin |
| Perfume |
| Water -qsp- |

*N, N-diethylaminopropyl-N²-alkyl asparagine (sodium salt) with the following formula:

$$R-NH-CH-COONa$$
$$\quad |$$
$$CH_2-CO-NH-(CH_2)_3-N\begin{matrix}C_2H_5\\ \\ C_2H_5\end{matrix}$$

R = the alkyl residue derived from the fatty acids of coprah and of tallow (⅔ coprah, ⅓ tallow)

During application of this depilatory, which was first packaged in a pressurized container, a very creamy foam emerged without any splatter. This foam had good wetting characteristics and adhered well to the skin.

We have found that the time for depilation is notably shortened as compared to depilatory foams which do not contain the combination of the amphoteric tensio-active agent and the tertiary amino oxide. After rinsing, the skin was smooth and perfectly free of hair.

EXAMPLE 6

A foaming hair straightener composition was prepared. The propellant used was the one described in Example 1. The percentage of the propellant was 11%. The nonpropulsive part of this foaming composition contained:

| Nonpropulsive part | | |
|---|---|---|
| Cetyl alcohol | 3 | g |
| Thiolactic acid | 7 | g |
| Lithium oxide | 4 | g |
| Triethanolamine | 3 | g |
| Glycerin | 0.85 | g |
| Amphoteric tensio-active agent* | 3 | g |
| Stearyldimethylamino oxide | 2 | g |
| Perfume | qs | |
| Water - qsp- | 100 | g |

*Composed according to the formula:

$$\begin{matrix}N=\!=\!=\!=\!CH_2\\ \|\quad\quad\quad|\\ R-C\quad\quad CH_2\\ \quad\setminus_+\swarrow\\ \quad\;N\\ \swarrow\;\setminus\quad Cl^-\\ NaOOCCH_2\quad CH_2CH_2OH\end{matrix}$$

formula in which R is the hydrocarbon residue derived from coparh; such a compound is sold by the REWO Society under the name of "STEINAPON AMC".

EXAMPLE 7

A foaming neutralizing composition was prepared for use as a neutralizer after the application of the hair straightener described in Example 6. The propellant used was the one described in Example 1, and its percentage was 4%. The nonpropulsive part of this foaming composition contained:

| Nonpropulsive part | |
|---|---|
| Potassium bromate | 9 g |
| Amphoteric tensio-active agent* | 2 g |
| Myristyldimethylamino oxide | 0.5 g |
| Distearyldimethylammonium chloride | 1.5 g |
| Tartaric acid -qsp- pH = 6 | |
| Perfume | qs |

-continued

| Nonpropulsive part | |
|---|---|
| Water -qsp- | 100 g |

*N,N-diethylaminopropyl-N²-alkyl asparagine (sodium salt) with the following formula:

$$R-NH-CH-COONa$$
$$\quad |$$
$$CH_2-CO-NH-(CH_2)_3-N\begin{matrix}C_2H_5\\ \\ C_2H_5\end{matrix}$$

R = the alkyl residue derived from fatty acids of coprah and of tallow (⅔ coprah, ⅓ tallow)

The application of the hair straightening foam obtained from the foaming composition of Example 6 was particularly convenient.

Due to the oiliness of this foam, it is very easy to see, and to localize the application perfectly. The foam penetrated easily into the mass of hair. After rinsing, the neutralizing foam of Example 7 was applied. Neutralization was in this way completed.

EXAMPLE 8

A foaming composition was prepared for use as a straightener of frizzled hair of the African type. The propellant used was the one described in Example 1. The percentage of the propellant is 8.5%. The nonpropulsive part of this foaming composition contains:

| Nonpropulsive part | | |
|---|---|---|
| Cetyl alcohol | 4 | g |
| Glycerin | 2 | g |
| Corn oil | 0.7 | g |
| Lithium oxide | 3 | g |
| Oxyethylene lanolin | 1.2 | g |
| Amphoteric tensio-active agent* | 0.3 | g |
| Lauryldimethylamino oxide | 0.4 | g |
| Perfume qs | | |
| Water qsp | 100 | g |

*Derived from fatty amines with betainic structure available commercially under the name of "DEHYTON AB 30".

The straightening foam obtained from this foaming composition permitted a very localized application.

It was thus possible to place the straightening product on the roots, without touching the scalp. The foam penetrated easily into the mass of hair.

Furthermore, after the necessary waiting time, the tensio-active agents favor the emulsion and the elimination of a supporting rinse. The hair was in a very beautiful cosmetic state.

The following are several examples of the new characteristics of the foams which are obtained from the foaming preparations of this invention.

EXAMPLE 9

Evidence of the Wetting Power of Foams:

A cup calibrated of 100 ml capacity, with a diameter at the base of 5 cm, was filled with foam and placed on a filter paper 15 cm in diameter.

The liquid which dripped from the foam impregnated the filter paper and formed a wet disk whose diameter enlarged with time. Thus, a foam with great wetting power causes a large absorption disk to be rapidly formed, while a foam with no wetting power causes no absorption zone.

In the following table, the wetting power of foams from Examples 1 and 3 is compared with a depilatory foam and a shaving foam of the usual type available commercially.

|  | Diameter of Absorbed Zones | | | | |
| --- | --- | --- | --- | --- | --- |
|  |  | 1 mn | 5 mn | 8 mn | 15 mn |
| Shaving foam (state of the art) | 5 cm | 5 cm | 5 cm | 5 cm | 5 cm |
| Depilatory foam (state of the art) | 5 cm | 5 cm | 5 cm | 5 cm | 5 cm |
| Foam Example 1 | 5 cm | 8 cm | 12 cm | 15 cm |  |
| Foam Example 3 | 5 cm | 7 cm | 11 cm | 15 cm |  |

Paralleling these tests, it was observed that the volume of foam from the composition of Examples 1 and 3 remained essentially constant, only the texture of the foam changed.

EXAMPLE 10

Evidence of the Draining Power of the Foams:

We filled with foam a calibrated cup of 90 ml capacity whose conical base was plugged with a fine nylon gauze permitting the liquid in the foam to drain into a graduated test tube. Then the volume of liquid that had flowed into the test tube was measured as a function of time.

In the following table, the draining powers of the foams of Examples 1 and 3 were compared with those which were obtained with the shaving foam and the depilatory foam of Example 9.

|  | Volume of Drained Liquid After | | | |
| --- | --- | --- | --- | --- |
|  | 2 mn 30 sec. | 5 mn | 10 mn | 15 mn |
| Shaving foam (state of the art) | 0 | 0 | 0 | 0 |
| Depilatory foam (state of the art) | 0 | 0 | 0 | 0 |
| Example 1 | 1 ml | 3 ml | 4.5 ml | 5 ml |
| Example 3 | 0.4 ml | 1 ml | 3 ml | 4 ml |

Paralleling these tests, it was observed that the volume of foam of the composition of Examples 1 and 3 remained essentially constant. Only the texture of the foam changed.

One can state, in view of these tests of Examples 8 and 9 that the foams of the compositions of Examples 1 and 3, according to the invention, possess a remarkable stability, allied with a wetting power, which is clearly superior to those of known foams presently in use.

What is claimed is:

1. An improved foaming composition in a pressurized container of the aerosol bomb type, to be dispensed in the form of a foam, said composition comprising from 2% to 14% propellant and a foaming product including from 0.2 to 6% of at least one amphoteric tensio-active agent and from 0.2 to 3% of at least one tertiary amino oxide, all the percentages above mentioned being expressed by weight in relation to the weight of the nonpropulsive part of the composition, the propellant used containing a mixture of liquified gas and of nitrous oxide saturating the aggregate of the liquid phase.

2. The composition of claim 1, wherein the mixture of liquified gas is saturated with $N_2O$, at an equilibrium pressure, after saturation, in the range of 4 to 8 bars.

3. The composition of claim 1 in which said liquified gas is selected from the group consisting of:
   a. mixture of dichlorodifluoromethane and dichlorotetrafluoroethane; and
   b. a mixture of dichlorodifluoromethane and dichlorotetrafluoroethane containing at least one nonhalogenated alkane selected from the group consisting of butane, propane, and isobutane;
   c. a mixture of butane and propane;
   d. a mixture of butane and propane and isobutane; and
   e. a mixture of isobutane and propane.

4. The composition of claim 3, wherein the relative proportions of the mixture dichlorodifluoromethane/dichlorotetrafluoroethane/alkane are between 0/100/0 and 25/25/50.

5. The composition of claim 3, wherein the relative proportions of the mixture butane/propane/isobutane are between 90/10/0 and 25/25/50.

6. The composition of claim 3, wherein the relative proportions of the mixture isobutane/propane are between 100/0 and 40/60.

7. The composition of claim 1, wherein the amphoteric tensio-active agent is taken from the group consisting of:
   a. agents of betainic structure;
   b. agents with imidazolic structure;
   c. agents with betainic imidazolic structure;
   d. agents with aminimide structure;
   e. agents with aminopropionate structure;
   f. agents with asparaginous structure corresponding to the following formula:

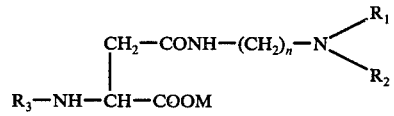

formula in which $R_1$ and $R_2$ are inferior alkyl radicals with up to 4 carbon atoms, $n$ is an integer with a value of 2 to 5, $R_3$ is an aliphatic hydrocarbon residue with from 10 to 18 carbon atoms and M is hydrogen, sodium, potassium or ammonium.

8. The composition of claim 1, wherein the tertiary amino oxide used is selected from the group consisting of alkyldimethylamino oxides, in which the alkyl radical is a lauric, cetylic, myristic or stearylic residue; the oxide of bi-(2-hydroxyethyl) coprahamine; and the oxide of bi-(2-hydroxyethyl) laurylmyristylamine.

9. The composition of claim 1 in which said composition is a cold hair permanent reducing solution which also contains, as its active product from 1 to 11% of at least one thiol and, by virtue of its foaming product from 0.2 to 6% of at least one of the amphoteric tensioactive agents and from 0.2 to 3% of at least one of the tertiary amino oxides, these percentages being expressed by weight in relation to the weight of the nonpropulsive part of the composition.

10. The composition of claim 9, wherein the thiol is selected from the group consisting of thioglycolic acid, thiolactic acid, thioglycerol and a mixture thereof.

11. The composition of claim 10, wherein the amount of thioglycolic acid is between 3% and 11%, the amount of thiolactic acid is between 1% and 6% and the amount of thioglycerol is between 4 and 8%, these percentages being expressed by weight in relation to the weight of the nonpropulsive part of the composition.

12. The composition of claim 1, wherein said composition is used in the treatment of hair and contains a permanent fixing solution, that contains, as the foaming product, from 0.2 to 6% of at least one of the amphoteric tensio-active agents, from 0.2 to 3% of at least one of the tertiary amino oxides, and from 0.15 to 2% of at least one cationic tensio-active agent and from 6 to 10 volumes of $H_2O_2$ or from 8 to 18% of potassium bromate or sodium bromate these percentages being expressed by weight in relation to the weight of the nonpropulsive part of the composition.

13. The composition of claim 1, which also contains, as active product, from 2 to 8% of at least one thiol neutralized in totality or in part and, as foaming product, from 0.5 to 2% of at least one of the amphoteric tensio-active agents and from 0.2 to 1.5% of at least one of the tertiary amino oxides, these percentages being expressed by weight in relation to the weight of the nonpropulsive part of the composition.

14. The composition of claim 13, wherein the thiol used is selected from the group consisting of thioglycolic acid, thiolactic acid, thioglycerol and a mixture of these.

15. The composition of claim 14, wherein the amount of thioglycolic acid in proportion to the nonpropulsive part is included between 2 and 7% by weight, the amount of thiolactic acid between 2 and 7% by weight and the percentage of thioglycerol between 3 and 8%.

16. The composition of claim 1, which contains, as foaming product, from 0.5 to 2% of at least one of the amphoteric tensio-active agents and from 0.2 to 1.5% of at least one of the tertiary amino oxides; and, as an active hair straightener agent from 4 to 10% of thioglycolic acid or of thiolactic acid, or from 1 to 5% of sodium hydroxide, lithium oxide or their mixture, these percentages being expressed by weight in relation to the weight of the nonpropulsive part of the composition.

17. The composition of claim 1, that contains, as foaming product, from 0.5 to 2% of at least one of the amphoteric tensio-active agents, from 0.2 to 1.5% of at least one of the tertiary amino oxides, from 0.5 to 1.5% of at least one of the cationic tensio-active agents; and, as an active hair neutralizing agent, from 3 to 10% of sodium bromate or potassium bromate, or from 6 to 10 volumes of $H_2O_2$, these percentages being expressed by weight in relation to the weight of the nonpropulsive part of the compound.

18. The composition of claim 12, wherein the cationic tensio-active agent used is selected from the group consisting of:
 a. the derivatives of quaternary ammonium; and
 b. the derivatives of pyridinium.

* * * * *